United States Patent
Yamasaki et al.

(10) Patent No.: US 6,299,885 B1
(45) Date of Patent: Oct. 9, 2001

(54) EXTERNAL PREPARATIONS CONTAINING WATERCRESS EXTRACT

(75) Inventors: Keiko Yamasaki; Tatsuya Konishi; Jutaro Shudo, all of Kagawa (JP)

(73) Assignee: Teikoku Seiyaku Co., Ltd., Kagawa (JP)

(*) Notice: Subject to any disclaimer, the term of this patent is extended or adjusted under 35 U.S.C. 154(b) by 0 days.

(21) Appl. No.: 09/254,877

(22) PCT Filed: Jul. 14, 1998

(86) PCT No.: PCT/JP98/03132

§ 371 Date: Dec. 15, 1999

§ 102(e) Date: Dec. 15, 1999

(87) PCT Pub. No.: WO99/03485

PCT Pub. Date: Jan. 28, 1999

(30) Foreign Application Priority Data

Jul. 18, 1997 (JP) ................................... 9-208299

(51) Int. Cl.⁷ .................. A61K 9/00; A61K 7/00
(52) U.S. Cl. ........................... 424/400; 424/401
(58) Field of Search .................. 424/489, 422, 424/195.1, 400, 401

(56) References Cited

U.S. PATENT DOCUMENTS 5,063,060 * 11/1991 Bernstein .......................... 424/422
5,296,225 * 3/1994 Adekunle et al. ................ 424/195.1

FOREIGN PATENT DOCUMENTS 57-53404 * 3/1982 (JP).
60013710 * 1/1985 (JP).
07025763 * 1/1995 (JP).

* cited by examiner

*Primary Examiner*—Thurman K. Page
*Assistant Examiner*—Blessing Fubara
(74) *Attorney, Agent, or Firm*—Crowell & Moring LLP

(57) ABSTRACT

The present invention relates to external preparations containing a watercress extract which are excellent in the humectant effect and also capable of reducing skin irritation and giving a comfortableness of use even if a calefacient is blended. In particular, the present invention provides the external preparations containing a watercress extract with which one or more members selected from the group consisting of powdered capsicum, capsicum extract, capsicum tincture, capsaicin and nonanoic acid vanillylamide can be blended as calefacients.

6 Claims, No Drawings

EXTERNAL PREPARATIONS CONTAINING WATERCRESS EXTRACT

TECHNICAL FIELD

The present invention relates to external preparations containing watercress extract giving a comfortableness of application with less irritation on the skin. In particular, the present invention relates to external preparations containing a solvent extract of watercress having the humectant effect on the application site of the said preparations. Additionally, even if calefacients are further contained, the preparations of the present invention are capable of reducing the uncomfortableness of these irritants and giving a comfortableness of use to the user.

BACKGROUND ART

Watercress (Nasturtium officinale) is a native European perennial plant which since introduced into Japan in the early Meiji era, has produced colonies in a clear stream as a naturalized plant, and it is eaten mainly as an ornamental accompaniment for Western cooking and as a vegetable for salads.

An attempt at blending various solvent extractions of plants including this watercress with external preparations such as cataplasms, ointments etc. is disclosed in Japanese Laid-Open Patent Application No. 7-25763. This publication describes that the combined use of kojic acid and/or its derivative having an inhibitory action on melanin formation and various plant extracts, brings about the effect of improving the persistent efficacy of kojic acid and/or its derivative while alleviating irritation on the skin. Under the present circumstances, however, it is not sufficiently examined whether the solvent extract of watercress when blended in the external preparations has the humectant effect or any other effects.

In recent years, as the house and office come to be completely furnished with air conditioners and by excess use of a soap or detergent, there are increasing skin troubles such as rough skin, itching etc. Against such symptoms, lotions or ointments containing urea or aloe extract etc. are commercially available as external preparations for efficiently maintaining the water content of the skin or giving the humectant effect. However, no adequate examination has been made of plant extract-blended external preparations excellent in the sense of use.

Meanwhile, calefacients such as powdered capsicum, capsicum extract, capsicum tincture, nonanoic acid vanillylamide etc. are known for a long time. If these calefacients are applied to the skin, the sense of heat is generated at the application site, blood capillaries are expanded to make blood circulation active to improve the metabolism of tissues, and demonstrate the anti-inflammatory and analgesic effects. Accordingly, there appeared the products containing these calefacients in cosmetics to utilize these effects or in medical external preparations the purpose of treating neuralgia, stiffshoulder, lumbago, rheumatism and so on.

However, when external preparations containing these calefacients are applied to the skin, there is a considerable difference in the degree in sense of heat, depending on the age, sex, application site and the individual conditions. Further, if the calefacient is contained in a large amount, it may cause the uncomfortable symptoms of skin irritation such as redness, rashes etc., therefore, it is difficult to determine the optimum concentration of the calefacients. Furthermore, if the calefacient is blended with plasters, the sense of irritation remains even after removal of the plasters, and severe pain is frequently experienced at the time of bathing.

To solve such problems, there is an attempt to give the mild sense of heat to the skin by using the herb medicines such as ginger, Japanese pepper etc. (see Japanese Patent Publication No. 56,206/1988). The other attempt is to relieve the irritation by containing perilla or yellow oak extract together with the calefacients (see Japanese Patent Publication No. 51,126/1988). However, even if these herb ingredients are contained, it cannot be said that the effect of reducing skin irritation while keeping the sense of heat is sufficient, so there is demand for further development.

Accordingly, in view of these circumstances, the object of the present invention is to provide external preparations containing herb ingredients, which are excellent in the humectant effect, capable of reducing the uncomfortableness of irritation even if calefacients are contained, and able to give a comfortableness of use to the user.

To solve the above mentioned problems, the present inventors extensively studied the humectant effect, and skin irritation relieving effect and the other effects of said preparations containing the herb ingredients. As a result, they found that external preparations containing solvent extract of watercress gives humectant to the skin, facilitates the sense of heat when calefacients are further contained, and hardly permit the calefacients to cause skin pain. Hence, the present inventors arrived at the completion of the present invention.

DISCLOSURE OF THE INVENTION

Accordingly, the embodiment of the present invention provides external preparations containing a solvent extract of watercress.

Another embodiment of the present invention provides external preparations further containing calefacients together with the solvent extract of watercress.

In the said embodiment, the present invention provides external preparations wherein the calefacient is one or more members selected from the group consisting of powdered capsicum, capsicum extract, capsicum tincture, capsaicin and nonanoic acid vanillylamide.

The preparations of the present invention are more specifically external preparations in which the drug form is an aqueous cataplasm, a plaster, an ointment, or a lotion.

The preferred embodiment of the present invention provides the aqueous cataplasm preparations for external application wherein the water content of the preparations is 30 to 80% by weight relative to the total weight of the adhesive gel base of the preparations, and the pH of said adhesive gel base is in the range of 3.0 to 9.0.

BEST MODE FOR CARRYING OUT THE INVENTION

The solvent extract of watercress used in the external preparations of the present invention can be prepared by extracting dried or intact leaves and stems of watercress, or intact watercress itself, with a solvent.

As used herein, the term "solvent" refers to hydrophilic organic solvents represented by water; lower alcohol such as methanol and ethanol; and polyhydric alcohol such as 1,3-butylene glycol, polyethylene glycol and propylene glycol, or mixtures thereof.

A process for producing said solvent extract of watercress can be done by using the following method as the topically example. That is, about 9 kg of 50% aqueous solution of 1,3-butylene glycol as the extraction solvent is added to 1 kg of the whole watercress or leaves and stems thereof, and the mixture is refluxed under heating at 100° C. for 1 hour and then cooled, and this solution is filtered to remove off the insoluble substances, and 50% aqueous solution of 1,3-butylene glycol is further added to the filtrate to adjust the total amount to 10 kg whereby the extract is obtained. Alternatively, 1 kg of the whole of watercress or leaves and stems thereof is immersed in about 9 kg of 50% aqueous solution of 1,3-butylene glycol as the extraction solvent at room temperature for 1 to 7 days or so, and then the insoluble substances are removed off by filtration. Then the additional extraction solvent is added to the filtrate to adjust the total amount to 10 kg.

As the solvent extract of watercress used in the external preparations of the present invention, the intact extract (hereinafter referred to as "watercress extract") produced by the method described above can be used. Furthermore, the dried extract substances obtained from the above watercress extract by the conventional techniques such as spray drying, freeze-drying etc. may also be used. Such dried extract diluted with suitable solvents such as purified water, lower alcohol and polyhydric alcohol further can be used for the external preparations of the present invention.

The amount of the solvent extract of watercress in the external preparations of the present invention is preferably 0.1 to 30% by weight, more preferably 0.5 to 10% by weight, when the watercress extract prepared according to the method illustrated above is used.

In the external preparations of the present invention, the calefacients can be contained together with the solvent extract of watercress. Said calefacients may be one or more members selected from powdered capsicum, capsicum extract, capsicum tincture, capsaicin and nonanoic acid vanillylamide. In particular, one or more members of capsicum extract, capsicum tincture, and nonanoic acid vanillylamide are preferably contained.

The amount of these calefacients contained in the external preparations of the present invention is preferably 0.001 to 5% by weight, more preferably 0.005 to 3% by weight relative to the total weight of the preparations.

The external preparations of the present invention with which these ingredients are suitably contained may be formulated into forms such as salves, cataplasms, liniments, lotions, ointments and plasters.

Besides those ingredients mentioned above, it is possible to contain vitamin E such as tocopherol acetate having promoting action on blood circulation; glycyrrhizic acid, dipotassium glycyrrhizinate and glycyrrhetic acid having analgesic and anti-inflamation action; diphenhydramine and chlorphenyramine maleate having anti-allergy action; and further plant extracts such as aloe extract, arnica extract, chamomile extract, and perilla extract, to the external preparations of the present invention.

Further, medical drugs frequently used in conventional external preparations such as glycol salicylate, methyl salicylate, camphor, menthol, peppermint oil, eucalyptus oil, turpentine oil, and so on can also be contained.

The amount of these drugs contained in the external preparations of the present invention is preferably 0.01 to 30% by weight, more preferably 0.1 to 15% by weight based on the total weight of the preparations.

The external preparations of the present invention suitably containing each of these components can be formulated into forms such as salves, cataplasms, liniments, lotions, ointments and plasters.

The base materials for the present preparations may be conventionally used ones for manufacturing the external preparations in this technical field.

For example, in the aqueous cataplasms, one or more water-soluble polymers selected from sodium alginate, gum Arabic, gelatin, pullulan, pectin, polyvinylpyrrolidone, polyvinyl alcohol, methylcellulose, ethylcellulose, sodium carboxymethylcellulose, hydroxyethylcellulose, hydroxypropyl-cellulose, polyacrylic acid, sodium polyacrylate, acrylic copolymers, maleiq anhydride copolymers and methyl vinyl ether are comprised. The amount of these polymers may be vary depending on the strength and cooling setting ability of the base materials or on workability at the time of manufacturing, but is usually 3 to 30% by weight based on the total weight of the adhesive gel base.

If the ingredients of the aqueous cataplasms base composed of such water-soluble polymers are to be cross-linked, the cross-linking agent, for example, polyvalent metals such as calcium chloride, magnesium chloride, aluminum chloride, aluminum sulfate, magnesium sulfate, calcium hydroxide, ferric hydroxide, aluminum hydroxide, calcium phosphate, aluminum stearate, magnesium stearate, calcium citrate, aluminum glycinal and so on, or polyethylene glycol diglycidyl ether, ethylene glycol diglycidyl ether, glycerin diglycidyl ether, triglycerin diglycidyl ether etc, can be used. The amount of these cross-linking agents is preferably 0.001 to 5% by weight, more preferably 0.005 to 3% by weight based on the total weight of the adhesive gel base.

Further, in the base material, it is possible to contain inorganic salts such as kaolin, bentonite, titanium oxide, zinc oxide etc. and polyhydric alcohols such as ethylene glycol, diethylene glycol, polyethylene glycol, propylene glycol, glycerin etc. The amount of these materials is preferably 5 to 65% by weight, more preferably 10 to 40% by weight, based on the total weight of the adhesive gel base.

The aqueous cataplasms as one embodiment of the external preparations provided by the present invention are water containing ones, and the water content of the aqueous cataplasms is desirably 30 to 80% by weight, preferably 35 to 75% by weight, more preferably 40 to 60% by weight based on the total weight of the adhesive gel base. If the water content is less than 30% by weight, the heat-sense effect of the calefacients cannot sufficiently be exhibited, whereas the water content exceeds 80% by weight, the shape retention of the cataplasms is lost, and as a result the adhesive gel base drips or remains at the time of release. Hence, these water contents are not preferable.

The pH value of the aqueous cataplasms is desirably adjusted to 3.0 to 9.0, preferably 3.5 to 8, more preferably 4 to 7. If the pH value of the adhesive gel base is less than 3.0, skin irritation occurs due to strong acidity, while the pH value exceeds 9.0, inconvenient actions such as skin corrosion and damage occur, so these pH values are not preferable.

In the ointments as another embodiment of the external preparations of the present invention, white vaseline, yellow vaseline, hydrogenated oil, solid paraffin, stearic acid, glycerin monostearate, glycerin trimyristate, cetyl alcohol, cetyl myristate, hydrocarbon gel, lanolin, polyacrylic acid and metallic salts thereof, cellulose derivatives, polyacrylic acid derivatives, polymethacrylic acid derivatives, natural gum such as gum Arabic and xanthan gum are used.

The amount of these materials may be vary depending on types of said ointments such as gel ointment, oil ointment and hydrophilic ointment, but usually in the range of 0.5 to 90% by weight.

In the ointments, it is also possible to contain purified water, lower alcohol such as ethanol, butanol etc., polyhydric alcohol such as glycerin, polyethylene glycol, 1,3- butylene glycol etc., isopropyl adipate, liquid paraffin, diethyl sebacate, squalane, squalene, vegetable oil, hydrogenated oil etc. The amount of these materials may usually be in the range of 1 to 90% by weight.

Further, it is possible to contain preservatives such as parahydroxybenzoate esters etc., antioxidants such as butyl hydroxy toluene etc., pH adjustors such as triethanolamine etc., surfactants such as glycerin monostearate, polyoxyethylene derivatives, sucrose fatty acid esters etc., coloring agent, perfumes etc.

These ingredients can be contained up to an amount of about 15% by weight at the maximum.

In the ointments of the present invention, the ingredients and the watercress solvent extract described above and the calefacients if deemed to be necessary, are mixed and formed in a conventional manner into oil ointment, hydrophilic ointment, gel ointment, and so on.

The plasters as further embodiment of the external preparations provided by the present invention, can be made by using of adhesives comprising synthetic rubber-based self-adhesives such as styrene-isoprene-styrene block copolymers, natural rubber-based self-adhesives, hydrogenated petroleum resin, rosin, hydrogenated rosin, terpene resin, acrylic self-adhesives, silicone-based self-adhesives, polyvinyl alcohol, polyvinylpyrrolidone, and so on.

The amount of the adhesives may be varied in the range of 15 to 80% by weight based on the total base adhesive material.

Further, said plasters may also contain liquid rubber such as polybutene, polyisobutylene etc., and softeners such as liquid paraffin, vegetable oil and lanolin etc. The amount of this softener may be varied in the range of 10 to 40% by weight based on the total weight of the base adhesive material. Further, it is possible to contain percutaneous absorption promoters in said plasters such as fatty acid esters, higher alcohol etc.

In said plasters, a backing may be laminated on the drug-containing self-adhesive layer (base adhesive material). Examples of such backing are resin films such as cellulose derivative films, polyethylene terephthalate film, nylon film, polyvinyl chloride film, polyethylene film, polyurethane film, polyvinylidene chloride film etc., and metallic sheets such as aluminum, and these are used alone or as a laminate with non-woven fabric etc.

The plasters of the present invention can be prepared in a usual manner by kneading and extending said ingredients, the solvent extract of watercress and if necessary the calefacients.

In the lotions as further additional embodiment of the external preparations of the present invention, an aqueous liquid such as normal water; purified water; lower alcohol for example ethanol, butanol and so on; polyhydric alcohol for example glycerin, propylene glycol, 1,3-butylene glycol and polyethylene glycol and so on, is used. The amount of the aqueous liquid may usually be varied in the range of 50 to 98% by weight based on the total weight of the preparations.

In said lotions, it is also possible to contain gum Arabic, sodium alginate, water-soluble cellulose lower alkyl ethers such as hydroxypropylcellulose, methylcellulose, hydroxyethylcellulose etc., carboxymethylcellulose and salts thereof, polyacrylic acid and salts thereof, suspending agents such as bentonite, surfactants such as glycerin monostearate, polyoxyethylene derivatives, sucrose fatty acid esters etc., preservatives such as paraoxybenzoate esters, coloring agent, and perfumes etc. These can be contained in an amount of about 15% by weight at the maximum.

The lotions of the present invention can be prepared in a usual manner using said ingredients, the solvent extract of watercress and if necessary the calefacients.

EXAMPLES

The external preparations of the present invention are described in more detail in references to the Examples and Comparative Examples; however, the present invention is not limited to those examples. Examples 1 to 7

Aqueous cataplasms bases having the compositions shown in Tables 1 and 2 below were prepared in a usual manner and then extended and applied in uniform thickness on non-woven fabric, and the surface was further covered with a polyethylene film, whereby the aqueous cataplasms in Examples 1 to 7 were obtained.

TABLE 1

Aqueous Cataplasm Formulations (No. 1)

| Ingredients | Amount (%) | |
|---|---|---|
| | Example 1 | Example 2 |
| Watercress extract | 3.0 | 5.0 |
| Sodium polyacrylate | 5.0 | 5.0 |
| Sodium carboxymethyl cellulose | 3.0 | 3.0 |
| Gelatin | 2.0 | 2.0 |
| Polyvinylpyrrolidone | 1.0 | 1.0 |
| Glycerin | 20.0 | 20.0 |
| Kaolin | 3.0 | 3.0 |
| Aluminum hydroxide | 0.8 | 0.8 |
| Tartaric acid | 0.8 | 0.8 |
| EDTA.2Na | 0.1 | 0.1 |
| Purified water | 61.3 | 59.3 |

TABLE 2

Aqueous Cataplasm Formulations (No. 2)

| Ingredients | Amount (%) | | | | |
|---|---|---|---|---|---|
| | Ex. 3 | Ex. 4 | Ex. 5 | Ex. 6 | Ex. 7 |
| Watercress extract | 1.0 | 3.0 | 1.0 | 3.0 | 5.0 |
| Capsicum tincture | 1.0 | 1.0 | | | 0.5 |
| Capsicum extract | | | 0.2 | 0.1 | |
| Nonanoic acid vanillylamide | 0.005 | 0.005 | | | 0.002 |
| Glycol salicylate | 1.0 | | 1.0 | 3.0 | 0.5 |
| dl-Camphor | 0.5 | 0.5 | 0.5 | 2.0 | 0.1 |
| Polyacrylic acid | 2.0 | 2.0 | 2.0 | 3.0 | 1.5 |
| Sodium polyacrylate | 5.0 | 5.0 | 5.0 | 7.0 | 3.0 |
| Sodium carboxymethyl celulose | 2.0 | 2.0 | 2.0 | 5.0 | 1.0 |
| Gelatin | 2.0 | 2.0 | 2.0 | 5.0 | 1.0 |
| Polyvinyl alcohol | 0.5 | 0.5 | 0.5 | 2.5 | 0.5 |
| Glycerin | 25.0 | 25.0 | 25.0 | 10.0 | 30.0 |
| Kaolin | 1.0 | 1.0 | 1.0 | 1.0 | 1.0 |
| Aluminum hydroxide | 0.6 | 0.6 | 0.6 | 0.6 | 0.3 |
| Tartaric acid | 0.4 | 0.4 | 0.4 | 0.4 | 0.2 |
| EDTA.2Na | 0.1 | 0.1 | 0.1 | 0.1 | 0.05 |
| Purified water | 57.895 | 56.895 | 58.7 | 57.3 | 55.348 |

Comparative Examples 1 to 5

Aqueous cataplasms bases having the compositions shown in Table 3 below were prepared in a usual manner, then extended and applied in uniform thickness on non-woven fabric, and the surface was further covered with a polyethylene film, whereby the aqueous cataplasms in Comparative Examples 1 to 5 were obtained.

TABLE 3

Comparative Example Formulations

| Ingredients | Comp. Ex. 1 | Comp. Ex. 2 | Comp. Ex. 3 | Comp. Ex. 4 | Comp. Ex. 5 |
|---|---|---|---|---|---|
| | | | Amount (%) | | |
| Japanese pepper extract | | | | 1.0 | |
| Perilla extract | | | | | 1.0 |
| Capsicum tincture | | 1.0 | 5.0 | 1.0 | 1.0 |
| Nonanoic acid vanillylamide | | 0.005 | | 0.005 | 0.005 |
| Glycol salicylate | | 1.0 | 1.0 | 1.0 | 1.0 |
| dl-Camphor | | 0.5 | 0.5 | 0.5 | 0.5 |
| Polyacrylic acid | | 2.0 | 2.0 | 2.0 | 2.0 |
| Sodium polyacrylate | 5.0 | 5.0 | 5.0 | 5.0 | 5.0 |
| Sodium carboxymethyl cellulose | 3.0 | 2.0 | 2.0 | 2.0 | 2.0 |
| Gelatin | 2.0 | 2.0 | 2.0 | 2.0 | 2.0 |
| Polyvinylpyrrolidone | 1.0 | | | | |
| Polyvinyl alcohol | | 0.5 | 0.5 | 0.5 | 0.5 |
| Glycerin | 20.0 | 25.0 | 25.0 | 25.0 | 25.0 |
| Kaolin | 3.0 | 1.0 | 1.0 | 1.0 | 1.0 |
| Aluminum hydroxide | 0.8 | 0.6 | 0.6 | 0.6 | 0.6 |
| Tartaric acid | 0.8 | 0.4 | 0.4 | 0.4 | 0.4 |
| EDTA.2Na | 0.1 | 0.1 | 0.1 | 0.1 | 0.1 |
| Purified water | 64.3 | 56.895 | 54.9 | 57.895 | 57.895 |

Example 8

According to the formulation shown below, capsicum tincture, nonanoic acid vanillylamide, watercress extract, glycol salicylate, dl-camphor, eucalyptus oil, propylene glycol, ethanol and purified water were uniformly mixed and dissolved whereby a lotion was obtained.

| | |
|---|---|
| Capsicum tincture | 1.0 g |
| Nonanoic acid vanillylamide | 0.01 g |
| Watercress extract | 3.0 g |
| Glycol salicylate | 1.0 g |
| dl-Camphor | 1.0 g |
| Eucalyptus oil | 0.3 g |
| Propylene glycol | 3.0 g |
| Ethanol | 60.0 g |
| Purified water | q.s. |
| Total | 100.0 g |

Example 9

According to the formulation shown below, capsicum tincture, watercress extract, glycol salicylate, propylene glycol, ethanol and purified water were uniformly mixed and dissolved whereby a lotion was obtained.

| | |
|---|---|
| Capsicum tincture | 5.0 g |
| Watercress extract | 25.0 g |
| Glycol salicylate | 1.0 g |
| Propylene glycol | 3.0 g |
| Ethanol | 40.0 g |
| Purified water | q.s. |
| Total | 100.0 g |

Example 10

According to the formulation shown below, capsicum tincture, watercress extract, methyl salicylate, dl-camphor, 1-menthol, carboxyvinyl polymer, triethanolamine, 1,3-butylene glycol, ethanol and purified water were uniformly kneaded whereby a gelled ointment was obtained.

| | |
|---|---|
| Capsicum tincture | 2.0 g |
| Watercress extract | 5.0 g |
| Methyl salicylate | 1.5 g |
| dl-Camphor | 0.5 g |
| 1-Menthol | 0.5 g |
| Carboxylvinyl polymer | 1.0 g |
| Triethanolamine | 0.5 g |
| 1,3-Butylene glycol | 3.0 g |
| Ethanol | 40.0 g |
| Purified water | q.s. |
| Total | 100.0 g |

Example 11

According to the formulation shown below, capsicum tincture, glycol salicylate, dl-camphor, glycerin monostearate and Polysorbate 80 were mixed uniformly with hydrogenated rape seed oil molten under heating at about 70° C., then hydrocarbon gel were added under cooling, and the mixture was further mixed whereby an ointment was obtained.

| | |
|---|---|
| Watercress extract | 10.0 g |
| Glycol salicylate | 20.0 g |
| dl-Camphor | 8.0 g |
| Glycerin monostearate | 5.0 g |
| Polysorbate 80 | 3.0 g |
| Hydrogenated rape seed oil | 10.0 g |
| Hydrocarbon gel | q.s. |
| Total | 100.0 g |

Example 12

According to the formulation shown below, nonanoic acid vanillylamide, watercress extract, glycol salicylate, dl-camphor, synthetic rubber, liquid rubber, and alicyclic saturated hydrocarbon resin were molten under heating and uniformly kneaded, then the mixture was extended on a support film whereby a plaster was obtained.

| | |
|---|---|
| Nonanoic acid vanillylamide | 0.01 g |
| Watercress extract | 5.0 g |
| Glycol salicylate | 5.0 g |
| dl-Camphor | 2.0 g |
| Synthetic rubber | 30.0 g |
| Polyvinyl alcohol | 2.0 g |
| Liquid rubber | 10.0 g |
| Alicyclic saturated hydrocarbon resin | 45.99 g |
| Total | 100.0 g |

Test Example 1

Test on the Skin Humectant Effect of Contained Watercress Extract

The aqueous cataplasms in Examples 1 and 2 and Comparative Example 1 were applied for 90 minutes on the upper arms of 20 volunteers and the state of their skin was evaluated after removal.

The results are shown in Table 4. The evaluation criteria are as follows. The effectiveness in Table 4 is expressed in terms of the proportion of volunteers for whom the cataplasms were effective, in which more than "+" evaluation criteria is considered to be effective, out of the 20 volunteers.

TABLE 4

Results of the Humectant Effect

|  | Example 1 | Example 2 | Comparative Example 1 |
|---|---|---|---|
| ++ | 1 person | 4 persons | 0 person |
| + | 10 persons | 11 persons | 3 persons |
| ± | 9 persons | 5 persons | 16 persons |
| − | 0 person | 0 person | 1 person |
| Effectiveness | 55% | 75% | 15% |

Evaluation criteria:
++: moist
+: slightly moist
±: no change
−: redness at the application site As is evident from the results shown in Table 4, it is understood that the aqueous cataplasms containing the watercress extract are superior in the humectant effect to the comparative preparation with which the extract was not contained.

Test Example 2

Test on the Heat Sense Irritation Effect of Contained Calefacient

The aqueous cataplasms in Examples 3 to 5 and Comparative Examples 2, 4 and 5 were applied to the upper arms of 10 volunteers and evaluated for heat-sense irritation in functional test.

The test results are shown in Table 5. The criteria for evaluation of heat-sense irritation are divided into the following 6 stage and expressed as the average of the 10 volunteers.

Evaluation criteria:
5: Very strong pain
4: Feels pain besides a sense of heat.
3: Feels a suitable sense of heat.
2: Feels a weak sense of heat.
1: Feels a sense of mere application.
0: Feels cold.

TABLE 5

Results of the Heat-Sense Irritation Effect Test

|  | After 10 min. | After 20 min. | After 30 min. | After 60 min. | After 90 min. |
|---|---|---|---|---|---|
| Example 3 | 1.1 | 2.4 | 3.1 | 3.3 | 3.2 |
| Example 4 | 1.2 | 2.6 | 3.4 | 3.4 | 3.4 |
| Example 5 | 1.6 | 3.0 | 3.5 | 3.7 | 3.6 |
| Comp. Ex. 2 | 0.4 | 0.8 | 1.6 | 2.2 | 1.8 |
| Comp. Ex. 4 | 1.0 | 2.4 | 2.6 | 2.6 | 2.4 |
| Comp. Ex. 5 | 0.8 | 2.0 | 2.3 | 2.5 | 2.3 |

As is evident from the results shown in Table 5 above, it is understood that the aqueous cataplasms of the present invention containing the watercress extract are strong in the sense of heat effect as compared with the comparative preparations with which the extract was not contained. Furthermore, the present aqueous cataplasms give a suitable sense of heat and are also superior in the sense of heat effect to even the preparations with which Japanese pepper extract or perilla extract was contained.

Test Example 3

Skin Irritation Test

The aqueous cataplasms in Examples 3 to 5, the lotion in Example 9, and the aqueous cataplasms in Comparative Examples 2 to 5 were applied for 90 minutes on the upper arms of 10 volunteers (provided that the cataplasms were removed thereafter) and observed for skin irritation (redness etc. at application site).

The results are shown in Table 6. The evaluation criteria are as follows.

TABLE 6

Results of Skin Irritation Test

|  | Example 3 | | Example 4 | | Example 5 | | Example 9 | |
|---|---|---|---|---|---|---|---|---|
|  | After 30 min. | After 60 min. | After 30 min. | After 60 min. | After 30 min. | After 60 min. | After 30 min. | After 60 min. |
| ++ | 0 | 0 | 0 | 0 | 0 | 0 | 0 | 0 |
| + | 0 | 0 | 0 | 0 | 0 | 0 | 0 |  |
| ± | 0 | 0 | 0 | 0 | 3 | 0 | 2 | 0 |
| − | 10 | 10 | 10 | 10 | 7 | 10 | 8 | 10 |

|  | Comparative Example 2 | | Comparative Example 3 | | Comparative Example 4 | | Comparative Example 5 | |
|---|---|---|---|---|---|---|---|---|
|  | After 30 min. | After 60 min. | After 30 min. | After 60 min. | After 30 min. | After 60 min. | After 30 min. | After 60 min. |
| ++ | 0 | 0 | 5 | 2 | 0 | 0 | 0 | 0 |
| + | 0 | 0 | 2 | 3 | 0 | 0 | 1 | 0 |
| ± | 2 | 1 | 2 | 4 | 2 | 1 | 2 | 0 |
| − | 8 | 9 | 1 | 1 | 8 | 9 | 7 | 10 |

Evaluation criteria:
−: Redness is not observed.
±: Faint redness is observed at the application site.
+: Redness is observed over the application site.
++: Redness is observed not only over the application site, but also around the application site.

As is evident from the results in Table 6, it is understood that the occurrence of skin irritation is low for the aqueous cataplasms or lotion of the present invention containing the watercress extract. Also the occurrence of skin irritation is low even in the case of the preparation in Example 9 with which the calefacient was contained in a large amount.

The occurrence of skin irritation is slightly inhibited in the case of the preparations in the Comparative Examples containing Japanese pepper extract or perilla extract, but this inhibition is not so great as that of the preparations of the present invention. Therefore, it is understood that the preparations of the present invention are superior in the effect of inhibiting skin irritation.

INDUSTRIAL APPLICABILITY

As described above, the external preparations of the present invention containing the solvent extract of watercress is excellent in the humectant effect, gives comfortable heat-sense stimulation even if a calefacient was further contained, and has the effect of reducing the occurrence of skin irritation, as compared to the conventional preparations with which Japanese pepper extract or perilla extract was contained.

Accordingly, the external preparations, giving a comfortableness of heat without giving an unconfortableness sense of irritation to the skin while being superior in the humectant effect on the skin, is provided by the present invention.

What is claimed is:

1. An external preparation consisting essentially of 0.1 to 30% by weight of a solvent extract of watercress based on the total weight of said preparation, wherein the drug form of said preparation is an aqueous cataplasm, a plaster, an ointment, or a lotion.

2. An external preparation containing a solvent extract of watercress and a calefacient, wherein the drug form of said preparation is an aqueous cataplasm, a plaster, an ointment, or a lotion.

3. The external preparations according to claim 2, wherein the calefacient is one or more members selected from the group consisting powdered capsicum, capsicum extract, capsicum tincture, capsaicin and nonanoic acid vanillylamide.

4. An aqueous cataplasm containing 0.1 to 30% by weight of a solvent extract of watercress based on the total weight of said aqueous cataplasm, wherein the water content of said aqueous cataplasm is 30 to 80% by weight relative to the total weight of an adhesive gel base and the pH of the adhesive gel base is in the range of 3.0 to 9.0.

5. An aqueous cataplasm according to claim 4, further comprising a calefacient.

6. An aqueous cataplasm according to claims 4 or 5, wherein said calefacient is selected from the group consisting of: powdered capsicum, capsicum extract, capsicum tincture, capsaicin, nonanionic acid vanillylamide, and mixtures thereof.

* * * * *